US007595052B2

(12) United States Patent
Saint-Remy et al.

(10) Patent No.: US 7,595,052 B2
(45) Date of Patent: Sep. 29, 2009

(54) COMPOSITION AND METHOD FOR THE PREVENTION AND/OR THE TREATMENT OF ALLERGY

(75) Inventors: Jean-Marie Saint-Remy, Grez-Doiceau (BE); Marc Jacquemin, Sart-Berhard (BE)

(73) Assignee: Collen Research Foundation, Leuven (BE)

( * ) Notice: Subject to any disclaimer, the term of this patent is extended or adjusted under 35 U.S.C. 154(b) by 556 days.

(21) Appl. No.: 10/221,955

(22) PCT Filed: Mar. 16, 2001

(86) PCT No.: PCT/BE01/00046

§ 371 (c)(1),
(2), (4) Date: Nov. 26, 2002

(87) PCT Pub. No.: WO01/70263

PCT Pub. Date: Sep. 27, 2001

(65) Prior Publication Data
US 2003/0129205 A1     Jul. 10, 2003

(30) Foreign Application Priority Data
Mar. 17, 2000   (GB)   ............................ 0006437.8

(51) Int. Cl.
*A61K 39/00*    (2006.01)
*A61K 39/35*    (2006.01)
*A61K 39/36*    (2006.01)
*A61K 38/00*    (2006.01)
*G01N 33/53*    (2006.01)
*A01N 37/18*    (2006.01)
*C07K 2/00*     (2006.01)
*C07K 4/00*     (2006.01)
*C07K 5/00*     (2006.01)
*C07K 7/00*     (2006.01)
*C07K 14/00*    (2006.01)
*C07K 16/00*    (2006.01)
*C07K 17/00*    (2006.01)

(52) U.S. Cl. .................. 424/185.1; 424/275.1; 435/7.1; 514/2; 530/300

(58) Field of Classification Search ........................ None
See application file for complete search history.

(56) References Cited

U.S. PATENT DOCUMENTS 6,090,386 A    7/2000   Griffith et al.

FOREIGN PATENT DOCUMENTS

| WO | WO 93/08279 | 4/1993 |
| WO | WO 95/17208 | 6/1995 |
| WO | WO 99/38978 | 8/1999 |
| WO | WO 00/50044 | 8/2000 |

OTHER PUBLICATIONS

Hervas-Stubbs et al. 'Therapeutic Vaccination of Woodchucks against Chronic Woodchuck Hepatitis Virus Infection.' Journal of Hepatology 27:726-737, 1997.*
Erhard et al. 'Adjuvant Effects of Various Lipopeptides and Interferon-gamma on the Humoral Immune Response of Chickens.' Poultry Science 79:1264-1270, 2000.*
Balsari et al. 'Antigen-specific immunodepression induced by doxorubicin-BSA conjugate in mice.' Int. J Immunopharmacol 13 (2-3) 155-158, 1991.*
Atwood et al. 'The Babel of Bioinformatics.' Science 290:471-473, 2000.*
Skolnick et al. 'From genes to protein structure and function: novel applications of computational approaches in the genomic era.' Trends in Biotechnology 18:34-39, 2000.*
Hoffman et al. Induction of an epitope-specific humoral immune response by lipopeptide-hapten conjugates: enhancement of the antimellittin response by a synthetic T helper (Th)-cell epitope. FEMS Immunol. Med. Microbiol. 17:225-234, 1997.*
Kohno et al. 'Genetic control of immune response to myoglobin. Ir gene function in genetic restriction between T and B lymphocytes.' J. Exp. Med. 156(5):1486-1501, 1982.*
Patent Abstracts of Japan & JP 10-259198. Connected T-Cell Epitope and its Use. Sep. 29, 1998.
Hervas-Stubbs. "Overcoming class II-linked non-responsiveness to hepatitis B vaccine". *Vaccine*, vol. 12, No. 10, pp. 867-871 (Aug. 1994).
Prieto et al. "Simple strategy to induce antibodies of distinct specificity: application to the mapping of gp120 and inhibition of HIV-1 infectivity". *European Journal of Immunology*. vol. 25, No. 4. pp. 877-883 (1995).
Wu et al. "Major T cell epitope-containing peptides can elicit strong antibody responses". *European Journal of Immunology*, vol. 30, No. 1, pp. 291-299 (Jan. 2000).
Wu et al. "Der p2 contains a naturally processed universal T cell epitope located within a conserved region". *Journal of Allergy and Clinical Immunology*, vol. 105, No. 1, pp. S154 (Jan. 2000).
Baldo. "Allergies to wheat, yeast and royal jelly: A connection between ingestion and inhalation". *Monographs in Allergy*, vol. 32, pp. 84-91 (1996).
Wu et al. "A naturally-processed universal T cell epitope is located within a conserved region of der p2: Implications for allergen sensitization and immunotherapy". *International Archives of Allergy and Immunology*, vol. 124, pp. 383-385 (2001).

(Continued)

*Primary Examiner*—Maher M Haddad
*Assistant Examiner*—Nora M Rooney
(74) *Attorney, Agent, or Firm*—Merchant & Gould P.C.

(57) ABSTRACT

The present invention is related to a method for modulating the immune system of a mammal patient towards an allergen, which comprises the step of inducing a pre-sensitisation of the immune system of said patient towards an immunogen carrying at least one T cell epitope homologous and functionally similar to an epitope present on said allergen and deriving from a naturally-occurring antigen in order to modify the response of said patient to a further sensitisation to said allergen, allowing that the immune response towards the allergen is modulated and that no allergy towards said allergen will be developed in said patient.

10 Claims, No Drawings

OTHER PUBLICATIONS

Wallner et al. "Immunotherapy with T-cell-reactive peptides derived from allergens". *Allergy*, vol. 49, pp. 302-308 (1994).
Liebers et al. "Overview of denominated allergens". *Clinical and Experimental Allergy*. vol. 26, pp. 494-516 (1996).
Bush. "Molecular biology of allergens", *Molecular Biology of Allergy and Immunology*, vol. 16, No. 3. pp. 535-563 (Aug. 1996).
Gupta et al. "Adjuvants-a balance between toxicity and adjuvanticity". *Vaccine*. vol. 11, Issue 3, pp. 291-306 (1993).
Johnson. "Molecular adjuvants and immunomodulators: New approaches to immunization". *Clinical Microbiology Reviews*. vol. 7, No. 3, pp. 277-289 (Jul. 1994).
Billerbeck et al., 2007, *World Journal of Gastroenterolgy*. vol. 13(36): 4858-4864 "Regulatory T Cells in viral hepatitis."
Hansen et al., 1999, *The Journal of Clinical Investigation*. vol. 103(2) 175-183 "Allergen-specific Th1 cells fail to counterbalance Th2 cell-induced airway hyperactivity but cause severe airway inflammation."

* cited by examiner

SEQUENCE LISTING

<160> NUMBER OF SEQ ID NOS: 2

<210> SEQ ID NO 1
<211> LENGTH: 11
<212> TYPE: PRT
<213> ORGANISM: Dermatophagoides

```
-continued

<400> SEQUENCE: 1

Ser Glu Pro Cys Ile Ile His Arg Gly Lys Pro
1               5                   10

<210> SEQ ID NO 2
<211> LENGTH: 13
<212> TYPE: PRT
<213> ORGANISM: Physeter catodon

<400> SEQUENCE: 2

Phe Ile Ser Glu Ala Ile Ile His Val Leu His Ser Arg
1               5                   10
```

COMPOSITION AND METHOD FOR THE PREVENTION AND/OR THE TREATMENT OF ALLERGY

FIELD OF THE INVENTION

The present invention is related to a composition and a method for modulating the immune response of a patient to an allergen and consequently preventing and/or treating allergy, especially airborne and foodborne allergies, as well as diseases of allergic origins.

STATE OF THE ART

Allergic diseases have a major impact on public health, with more than 20% of the general population affected by at least one form of allergic manifestations, such as rhinitis, bronchial asthma, atopic eczema or systemic anaphylaxis to drugs or insect stings.

Allergy, which is also called immediate hypersensitivity, is mediated by specific antibodies belonging to the IgE isotype. The mechanisms by which an allergic reaction develops are well elucidated, but the factors predisposing to allergy are poorly understood, as well as the factors governing the evolution during aging.

The manifestations of allergy often evolve from atopic eczema in infancy to airway hypersensitivity and bronchial asthma in later infancy and childhood. Atopic eczema is thought to be at least partly related to the development of allergy to food antigens, while allergic asthma is by definition triggered by sensitization to airborne allergens.

Whether sensitization to food- and airborne allergens represent two independent manifestations of an allergic status, namely a predisposition to produce IgE antibodies to common antigens, or whether the two phenomena are linked together is unknown.

Current treatment of allergic symptoms include allergen avoidance, drug therapy and immunotherapy. Complete avoidance from allergen exposure is the most logical approach, but it remains very difficult, or even impossible, to achieve in most cases. Drug therapy is useful, but alleviates symptoms without influencing their causes. In addition, drug treatment is usually limited by undesirable side-effects.

There are currently different approaches for immunotherapy. Among these approaches is conventional hyposensitisation which is a treatment consisting in administering to the patient progressively increasing doses of the allergen(s) to which said patient has developed a sensitivity.

Another approach consists in altering the physico-chemical properties of the allergen in order to reduce recognition by specific antibodies, IgE in particular.

It is also possible to use allergen-derived peptides. Such peptides are presented by antigen-presenting cells to specific T cells in a manner which results in induction of T cell unresponsiveness, or anergy. Under such circumstances no specific IgE antibodies are produced. Patent application WO 93/08279 gives an example of such allergen-derived peptides One human application of this concept is the administration of a peptide derived from the sequence of T cell epitopes present on the Fel dI allergen, by subcutaneous injections in cat-sensitive individuals (Wallner B. P & Gefter M L (1994), Allergy 49, 302-308).

It is also possible to prevent the release of the mediators responsible for allergic manifestations by interfering in the activation signal provided to mast cells or basophils by cross-linking surface IgE antibodies. This can be achieved by using molecules presenting only one IgE binding epitope, or peptides that interfere in the recognition of IgE antibodies by the alpha chain of the high-affinity receptor.

Other methods for treating and/or preventing hypersensitivity to allergens are disclosed, for example, in documents WO 00/50044 and U.S. Pat. No. 6,090,386.

AIMS OF THE INVENTION

The present invention aims to provide a new composition and method for modulating and modifying the immune response of a patient to an allergen and consequently providing alternative methods and means for preventing and/or treating allergy, especially airborne and foodborne allergies, as well as diseases of allergic origins.

More particularly, the present invention aims to provide such method and means which are safe and can be easily monitored and controlled.

DEFINITIONS

The following definitions are given in order to make clear the description of the present invention.

It is meant by "antigen" a structure of a macromolecule, preferably made of proteic composition but also made of one or more hapten(s), and comprising "epitopes".

It is meant by "food or pharmaceutical antigen", an antigenic structure preferably of proteinic and/or polysaccharidic composition, naturally available in a food component or a pharmaceutical product including a vaccine.

It is meant by "epitope", one or several portions (which may define a conformational epitope) of an antigen or an immunogen which are specifically recognized and bound by an antibody or a portion thereof (Fab', Fab2', etc.) or a receptor presented at the cell surface of a B or T cell lymphocyte, and which is able by said binding to induce an immune response.

More particularly, it is meant by "T cell epitope" an epitope which is specifically recognized and bound by a receptor at the cell surface of a T lymphocyte.

It is meant by "immunogen" a food or pharmaceutical antigen which is able as a whole to trigger both a humoral and a cellular immune response.

It is meant by "atopy", a predisposition (partly of genetic origin) of an individual patient having an immune system producing an excess of antibodies belonging to the IgE isotype in response to allergens. Individuals presenting such characteristics are therefore called "atopics".

An "allergen" is defined as a substance, usually a macromolecule of proteic composition, which elicits the production of IgE antibodies in predisposed, preferably genetically disposed, individuals (atopics) patients.

Similar definitions are presented in the following references: *Clin. Exp. Allergy*, No. 26, pp. 494-516 (1996); *Mol Biol. of Allergy and Immunology*, ed. R. Bush, Immunology and Allergy Clinics of North American Series (August 1996)

These allergens are preferably the main allergens which are selected from the group consisting of:

- food allergens present in peanuts, codfish, egg white, soybean, shrimp, milk and wheat,
- house dust mites allergens obtained from Dermatophagoides spp. pteronyssinus, farinae and microceras, *Euroglyphus maynei* or *Blomia*,
- allergens from insects present in cockroach or hymenoptera,
- allergens from pollen, especially pollens of tree, grass and weed, allergens present in animals, especially in cat, dog, horse and rodent, allergens present in fungus, especially from *Aspergillus*, *Alternaria* or *Cladosporium*, and occupational allergens present in such products as latex, amylase, etc.

Said allergens can also be main allergens present in moulds or various drugs such as hormones, antibiotics, enzymes, etc. (See also the definition in Clin. Exp. Allergy no.26, p:494-516 (1996) and Mol. Biology of Allergy and Immunology, Ed. R. Bush (August 1996)).

"Allergy" is the ensemble of signs and symptoms observed whenever an atopic individual patient encounters an allergen to which he has been sensitised, which may result in the development of various diseases, in particular respiratory diseases and symptoms such as bronchial asthma.

"Hypersensitivity" is an untoward reaction produced in an individual upon exposure to an antigen to which it has become sensitised; "immediate hypersensitivity" depends of the production of IgE antibodies and is therefore equivalent to allergy.

The wording "proteins phylogenetically unrelated" refers to proteins for which no evolutionary link can be established.

SUMMARY OF THE INVENTION

The present invention is related to a method for modulating (modifying the reactivity of) the immune system of a mammal patient (including a human) towards an allergen, said patient being preferably an atopic patient Said method comprises the step of inducing a pre-sensitization of the immune system (through contact with immune cells (APC) of said patient) towards an immunogen derived from a naturally occurring antigen (which means an immunogen present in a food or pharmaceutical component), in order to modify the immune response to a further sensitization to said allergen, such that the immune response towards the allergen is modulated (preferably decreased in order to change the atopy behaviour of the patient), no allergy towards said allergen develops in said patient or said allergy decreases and said patient is rendered non-allergic.

The inventors have observed that it is possible to modify the reactivity of the immune system towards said allergen (render said patient non-allergic), because they have identified that an immunogen deriving (obtained) from a naturally occurring antigen (presented in a food or pharmaceutical product), could carry a T cell epitope homologous and functionally similar to an epitope present on said allergen.

It is meant by an homologous T cell epitope presented in an immunogen, a T cell epitope having an amino-acid sequence which presents more than 40%, preferably more than 50%, more preferably more than 60% homology (or sequence identity) with the corresponding epitope sequence presented in an allergen.

The T cell epitope present on said allergen and the T cell epitope present on the immunogen are recognised by the same T cells, in particular by T cell clones. They could therefore be used alternatively for modulating the immune response by one compound against another.

The above-mentioned T cell epitope carried by the immunogen is preferably a universal T cell epitope, preferably present upon an airborne allergen or a foodborne allergen.

Preferably said allergen is selected from the group consisting of rhino-sinusitis allergens, allergic bronchial asthma allergens and atopic dermatitis allergens.

Preferably said allergen is the Der p II protein and the corresponding universal T cell epitope corresponds to SEQ ID NO. 1.

According to the invention, the immunogens are preferably derived (obtained) from myoglobin protein and the corresponding identified epitope of myoglobin is preferably SEQ ID NO. 2.

The method according to the invention comprises also the step of administrating, preferably to said mammal patient including humans, a sufficient amount of a pharmaceutical composition comprising said immunogens or the above-mentioned epitopes of said immunogens and a pharmaceutical adequate carrier suitable for an administration to said patient. The pharmaceutical adequate carrier can vary according to the type of administration (oral administration, parental administration, intravenous or intradermal administration, etc.).

Therefore, another aspect of the present invention is related to a pharmaceutical composition comprising said immunogen, an epitope of said immunogen (possibly combined with a carrier molecule such as BSA) and a pharmaceutically adequate carrier suitable for an administration.

Said pharmaceutical composition may comprise also one or more adjuvants which will modulate the immune response of the patient.

Adjuvants can be in any form suitable for administration in human beings. Examples of adjuvants are oil emulsions of mineral or vegetal origin, mineral compounds such as aluminium phosphate or hydroxide, or calcium phosphate, such as alum, incomplete Freund's adjuvant, heparin, lyposin, saponin, squalene. Recent reviews on adjuvants for human administration are descried by Gupta R. K. et al., (*Vaccine* 11, pp 293-306 (1993)) and by Johnson A. G. (*Clin. Microbiol. Rev.* 7, pp 277-289 (1994)).

The pharmaceutical composition according to the invention is prepared by the methods generally applied by the man skilled in the art, for the preparation of various pharmaceutical compositions, especially vaccines, wherein the percentage of the active compound/pharmaceutical acceptable carrier can vary within very large ranges (generally a suitable dosage unit form contains about 0.005 mg to about 1 mg of compound per kg/body weight of patient), only limited by the tolerance of the patient to the compound, in particular by the frequency of administration, and by the specific allergies and the symptoms to be treated.

Preferably, the active compound comprising the immunogen is present in the pharmaceutical composition in a concentration which allows at least the reduction or the suppression of the signs and symptoms of allergy or of a disease of allergic origin.

Said pharmaceutical composition could be also a vaccine suitable for treating or preventing allergy, especially airborne and foodborne allergy, as well as diseases of allergic origin. Therefore, a more specific aspect concerns said pharmaceutical composition for use as a medicament, especially for treating and/or preventing allergy, airborne and foodborne allergies as well as diseases of allergic origin.

The present invention is also related to a method comprising the step of administrating to a mammal patient, including a human, a sufficient amount of said pharmaceutical composition for reducing or suppressing the symptoms of allergy.

A last aspect of the present invention is related to the use of said pharmaceutical composition for the manufacture of a medicament in the prevention and/or the treatment of allergy, especially airborne and foodborne allergies and diseases of allergic origin.

EXAMPLE 1 OF THE INVENTION

Der p II is a main, ubiquitous protein which belongs to Group 2 allergens derived from house dust mites (see for instance Bush R K., Molecular biology of allergens, in Molecular biology of allergy and immunology, Immunology and Allergy Clinics of North America, vol 16, 3, pp 535-563, 1996). The latter are involved in allergic sensitization of more than 70% of subjects suffering from respiratory allergy, i.e. rhino-sinusitis and/or bronchial asthma.

In the course of studies on the immunogenicity of this allergen, the Inventors have identified a major T cell epitope on Der p II, which is recognized by virtually all individuals within a animal species. The sequence of this epitope is SEPCIIHRGKP and will be called hereinafter "SEQ ID NO. 1".

A search for sequence homology identified another universal T cell epitope, called hereinafter "FIS" or "SEQ ID NO. 2", derived from sperm whale myoglobin, the sequence of which is FISEAIIHVLHSR (homologous residues are underlined). SEQ ID NO. 1 and SEQ ID NO 2 are phylogenetically unrelated. Myoglobin is the red pigment which constitutes the oxygen reservoir of muscle cells and as such is a major constituent of meat.

In order to determine experimentally whether this sequence homology could result in functional cross-reactivity between Der p II and myoglobin, mice were immunized by subcutaneous injections of FIS (SEQ ID NO. 2) or myoglobin.

The FIS (or SEQ ID NO. 2) peptide was obtained by synthesis. Sheep myoglobin was purchased from Sigma Chemicals (St-Louis, Mich.).

Balb/c mice (H-$2^d$) were injected once in the footpad with 50 μl of a solution containing 100 μg of peptide or myoglobin emulsified in complete Freund's adjuvant. Ten days later, regional lymph nodes were retrieved, teased and extensively washed with sterile saline to recover cells. The cell suspension was then washed in RPMI buffer (Gibco). Pure CD4$^+$ T cell suspensions were obtained by negative selection using antibodies towards CD45R, CD11b and CD11c, all conjugated to magnetic beads according to the manufacturer's instructions (Miltenyi Biotech GmbH, Germany).

Functional cross-reactivity between Der p II, FIS and myoglobin was checked by in vitro proliferation assays. Thus, the T cell suspension was adjusted to $5 \times 10^6$ cells per ml in RPMI 1640 buffer supplemented with 2 mM glutamine, 100 U penicillin/ml, 100 μg streptomycin/ml, 5% heat-inactivated fetal calf serum and $5 \times 10^{-5}$ M 2-mercaptoethanol. One hundred μl of the T-cell-enriched fraction ($4 \times 10^5$ cells per well) was cultured in 100 μl of the above-described medium containing different concentrations of test peptide or myoglobin, and mitomycin-C treated syngeneic naive spleen cells as a source of APC ($4 \times 10^5$ per well). Incubation was carried out into a humidified atmosphere of 5% $CO_2$ in air for 4 days, and cells were pulsed during a final 18-h incubation with 1 μCi of [$^3$H] thymidine per well. The cells were then harvested onto glass fibres using a multiple-cell harvester. Radioactivity incorporated into proliferating cells was determined in a liquid scintillation counter. All tests were carried out in triplicate. The proliferative response was expressed as c.p.m.$\times 10^3$ after subtracting background value incorporation in the absence of antigen.

The results showed that T cells from FIS- and myoglobin-immunized mice proliferated to myoglobin and to Der p II. It has been shown that the FIS peptide, as well as myoglobin, are immunogen.

As FIS is an epitope of sperm whale myoglobin, the Inventors have checked whether other myoglobin molecules contain close or identical sequences.

A high homology was found for bovine (81%), sheep (82%), goat (80%) and human myoglobin as determined from the consultation of gene databanks (SWISSPROT protein database).

The Der p II T cell epitope, SEQ ID NO. 1, described here was shown to be recognised in the context of three additional mouse H-2 haplotypes other than (H-$2^d$) haplotype, as well as by a significant proportion of human subjects (more than 85%).

For mouse T cells, a procedure identical to that described above was used with mice pertaining to the H-$2^b$ (C57BL/6 strain), H-$2^k$ (C3H strain) and H-$2^d$ (SJL strain). A significant proliferative response was observed for the three haplotypes.

Moreover, T cells were prepared from the peripheral blood of atopic individuals. Thus, a 50-ml sample of peripheral blood was obtained in heparin. The blood sample was diluted vol/vol in RPMI 1640 and applied to a Ficoll-Hypaque density gradient. After a 30 min centrifugation, cells from the interface were collected and washed in RPMI 1640. The cell pellet was finally resuspended in RPMI supplemented with 10% AB+ human serum, 80 μg/ml gentamycine, 2 mM L-glutamine and 18 mM D(+)-glucose. Proliferation assays was then carried out as described above for mouse cells, except that the various concentrations of FIS peptide or myoglobin were added immediately to the cell suspension.

Taken altogether, the obtained results indicate that the phenomenons observed in an animal species are relevant to human beings.

These results show that significant structural and functional cross-reactivity can exist between two phylogenetically totally unrelated proteins and that sensitization to one of such proteins, or to a part of such protein containing an immunogen, can modulate the immune response towards the other. Thus, a food antigen (myoglobin), or a portion of it containing the appropriate immunogen, can modulate sensitization to an airborne allergen (Der p II).

The invention claimed is:

1. A method for the treatment of allergy comprising the step of administrating a sufficient amount of a pharmaceutical composition comprising adequate pharmaceutical carrier and an immunogen to a mammal patient for decreasing or suppressing the symptoms of an allergy or a disease of allergic origin induced by immune response to an allergen comprising SEQ ID NO:1, and wherein said immunogen consists of a T cell epitope identified by SEQ ID NO: 2.

2. The method of claim 1, wherein the allergen is airborne or foodborne.

3. The method according to claim 1, wherein the T cell epitope identified by SEQ ID NO:2 is present upon a carrier molecule.

4. The method according to claim 3, wherein the carrier molecule is BSA.

5. The method according to claim 1, wherein the allergen is the Der p II protein having the T-cell epitope identified by SEQ ID NO 1.

6. The method of claim 1, wherein the pharmaceutical composition is administered to pre-sensitize said patient against said allergen.

7. The method of claim 1, wherein treatment of allergy comprises pre-sensitization of the immune system of the mammal patient.

8. A method of decreasing the immune response of a mammal towards a Der p II allergen comprising SEQ ID NO:1, said method comprising:

inducing pre-sensitization of the immune system to Der p II allergen in a mammal in need thereof by administering to said mammal a sufficient amount of a pharmaceutical composition comprising an adequate pharmaceutical carrier and an immunogen consisting of a T cell epitope identified by SEQ ID NO:2 thereby decreasing the immune response of said mammal towards said Der p II allergen;

wherein said immune response towards subsequent exposure to said Der p II allergen is modulated such that signs and symptom of allergy towards said allergen are reduced in said mammal.

9. A method of decreasing the immune response of a mammal towards a Der p II allergen comprising SEQ ID NO:1, said method comprising:

inducing pre-sensitization of the immune system to Der p II allergen in a mammal in need thereof by administering to said mammal a sufficient amount of a pharmaceutical composition comprising an adequate pharmaceutical carrier and an immunogen consisting of a T cell epitope identified by SEQ ID NO:2 thereby decreasing the immune response of said mammal towards said Der p II allergen;

wherein said immune response towards subsequent exposure to said Der p II allergen is modulated such that signs and symptom of a disease of Der p II allergic origin are reduced in said mammal.

10. The method of claim 7, wherein said mammal is human.

* * * * *